United States Patent [19]
Osypka

[11] Patent Number: 4,774,951
[45] Date of Patent: Oct. 4, 1988

[54] SURGICALLY IMPLANTABLE CARDIAC PACEMAKER

[76] Inventor: Peter Osypka, Basler Strasse 109, D-7889 Grenzach-Wyhlen, Fed. Rep. of Germany

[21] Appl. No.: 875,276

[22] Filed: Jun. 17, 1986

[30] Foreign Application Priority Data

Jun. 19, 1985 [DE] Fed. Rep. of Germany ....... 3521874

[51] Int. Cl.[4] .............................................. A61N 1/36
[52] U.S. Cl. ........................... 128/419 P; 128/419 PG
[58] Field of Search ................ 128/419 PG, 784, 785, 128/786, 419 P, 348.1; 604/891

[56] References Cited

U.S. PATENT DOCUMENTS

| | | | |
|---|---|---|---|
| 3,951,147 | 4/1976 | Tucker et al. ........................ | 604/891 |
| 4,142,532 | 3/1979 | Ware ................................ | 128/419 P |
| 4,146,029 | 3/1979 | Ellinwood .......................... | 604/891 |
| 4,365,639 | 12/1982 | Goldreyer ..................... | 128/419 PG |
| 4,461,194 | 7/1984 | Moore ............................. | 128/419 P |
| 4,479,489 | 10/1984 | Tucci .............................. | 128/419 P |

*Primary Examiner*—William E. Kamm
*Assistant Examiner*—Timothy Keegan
*Attorney, Agent, or Firm*—Peter K. Kontler

[57] ABSTRACT

The output or outputs of the subcutaneously implanted pulse generator of a cardiac pacemaker are accessible by introducing a cannula or the wire of a stylet through the skin and thereupon through a silicone membrane which is implanted beneath the skin and surrounds a portion of a chamber which contains the output or outputs or affords access to the output or outputs through a conduit or conductor. The cannula or the wire of the sylet can be used to test the pulse generator, the lead or leads and/or the connection or connections between the lead or leads and the pulse generator as well as to admit medicaments and/or to facilitate or carry out adjustments or repairs.

23 Claims, 8 Drawing Sheets 4,774,951

SURGICALLY IMPLANTABLE CARDIAC PACEMAKER

BACKGROUND OF THE INVENTION

The invention relates to improvements in surgically implantable cardiac pacemakers. More particularly, the invention relates to improvements in pacemakers of the type having a subcutaneously implantable pulse generator and one or more pulse transmitting leads extending from the pulse generator to the heart of the patient.

Cardiac pacemakers of the type to which the present invention pertains are disclosed, for example, in U.S. Pat. No. 3,198,195 to Chardack. Surgically implantable pulse transmitting leads are disclosed in U.S. Pat. No. 4,393,883 to Smyth et al. A drawback of the patented pacemakers and of other presently known implantable pacemakers is that any, even minor, failure of the pulse generator and/or of the leads necessitates complex and often painful and expensive surgery. The implanted parts of a cardiac pacemaker are bound, or at least likely, to fail and each such failure necessitates a lengthy and careful examination of the patient in order to ascertain the cause and/or extent of the failure. For example, the energy source or sources of the pulse generator are likely to be exhausted earlier than anticipated, the electric circuitry of the pulse generator can develop a short or another defect, or the tips of the electrodes which are implanted in the heart of the patient become dislodged with attendant intensification or weakening of the transmitted pulses. The implanted pacemaker is further likely to develop sensing problems which can involve a failure to properly synchronize the cardiac pulses with those which are transmitted by the pulse generator.

The situation is aggravated if the implanted pacemaker develops defects which are of intermittent nature and/or which do not induce the patient to develop clear-cut reactions. In accordance with heretofore known techniques, intermittent or non readily detectable failures of the implanted pacemaker necessitate complete removal of the pulse generator and/or pulse transmitting lead or leads from the patient's body with attendant risks and problems which are invariably involved in carrying out such delicate surgery.

OBJECTS AND SUMMARY OF THE INVENTION

An object of the invention is to provide a novel and improved subcutaneously implantable cardiac pacemaker which is constructed and which can be implanted in such a way that many of its component parts are readily accessible for monitoring, adjustment and/or repair while remaining implanted in the body of the patient.

Another object of the invention is to provide a cardiac pacemaker which can be tested, adjusted and/or repaired in a simple, time-saving and inexpensive way without surgery.

A further object of the invention is to provide a novel and improved method of monitoring and/or adjusting the operation of a subcutaneously implanted cardiac pacemaker.

An additional object of the invention is to provide the cardiac pacemaker with novel and improved means for affording access to the parts of the pulse generator as well as to the parts of one or more pulse transmitting leads.

The improved cardiac pacemaker comprises a subcutaneously implantable pulse generator having at least one pulse transmitting output, and at least one subcutaneously implantable penetrable wall. The output or outputs of the pulse generator are accessible to a percutaneous instrument (such as an electric conductor or a cannula) in response to penetration of such instrument first through the skin of the user of the pacemaker and thereupon through the penetrable wall. The pacemaker further comprises at least one implanted pulse transmitting lead which is connected to the pulse generator to receive pulses from the output.

The wall can consist of or can contain a self-sealing material and can include or constitute a membrane whose material is neutral so that it is compatible with the human body as an environment. The membrane can consist of or it can contain silicone, and the wall can comprise means for reinforcing the membrane and for maintaining it in the body in a preselected implanted position. The reinforcing means can comprise a marginal bead. The thickness and/or the material of the wall can be selected in such a way that the wall is substantially rigid and tends to assume and retain a predetermined shape.

The wall can form part of or it can be connected with the housing of the pulse generator in such a way that the housing and the wall define at least one chamber for the output or outputs of the pulse generator. The wall seals the chamber or chambers from the surrounding body tissue. Such pacemaker can employ one or more subcutaneous pulse transmitting leads having open ends which communicate with the chamber or chambers.

The housing of the pulse generator can include an electrically conductive portion which is accessible to the instrument upon penetration of the instrument through the wall, and the aforementioned lead or leads are electrically connected with the output or outputs and/or with the conductive portion of the housing. The conductive portion can comprise a metallic plate, a metallic netting or a metallic latticework. The conductive portion of the housing and the wall can define the aforementioned chamber or chambers affording access to the output or outputs of the pulse generator. The chamber can be disposed between a terminal of the lead and the output of the pulse generator, particularly between the output and a connecting means (such as a separable plug-and-socket connection) which is used to separably connect the lead to the housing of the pulse generator. The latter can comprise a funnel-shaped portion defining a narrowing passage which extends from the chamber to the connecting means.

The wall can be spaced apart from the pulse generator, and the pacemaker then further comprises a casing or other suitable means defining with the wall a chamber which is accessible to an instrument upon penetration through the skin and thereupon through the wall. Such pacemaker further comprises means (e.g., one or more electrical conductors and/or one or more conduits) for connecting the chamber with the pulse generator. The terminal or terminals of one or more pulse transmitting leads are then accessible to an instrument which has penetrated through the wall.

In accordance with a presently preferred embodiment of the invention, the pacemaker can comprise a plurality of subcutaneously implantable penetrable walls and a subcutaneous pulse transmitting lead for each wall. The leads have terminals which are accessible to an instrument upon penetration of the instrument through the skin of the patient and thereafter through the respective penetrable walls.

The novel features which are considered as characteristic of the invention are set forth in particular in the appended claims. The improved pacemaker itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
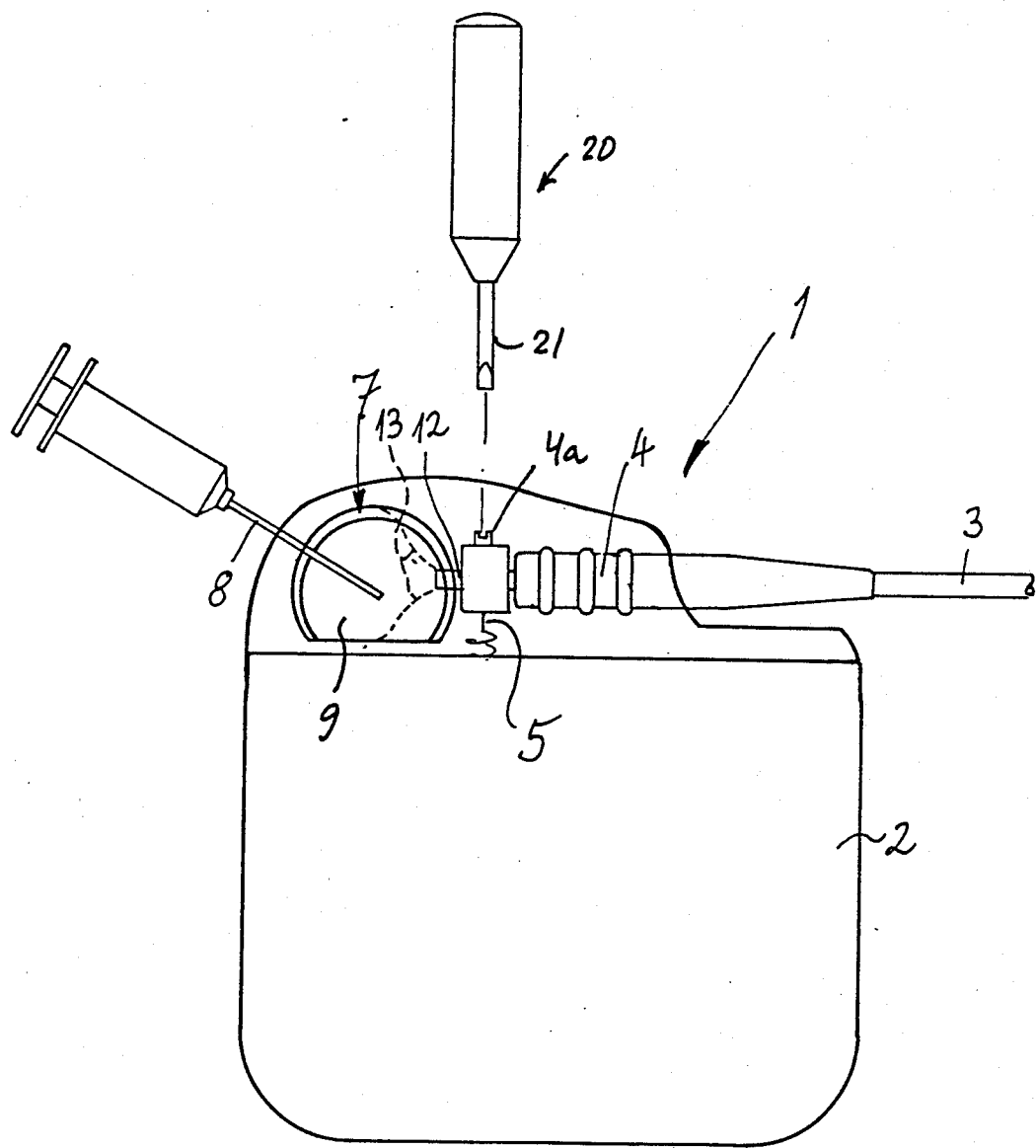
FIG. 1 is a schematic elevational view of a cardiac pacemaker with a single penetrable wall and a single pulse transmitting lead, further showing a cannula which can be caused to penetrate through the wall and a screwdriver which can be used to establish or to terminate the connection between the lead and the output of the pulse generator.
Figure 5:
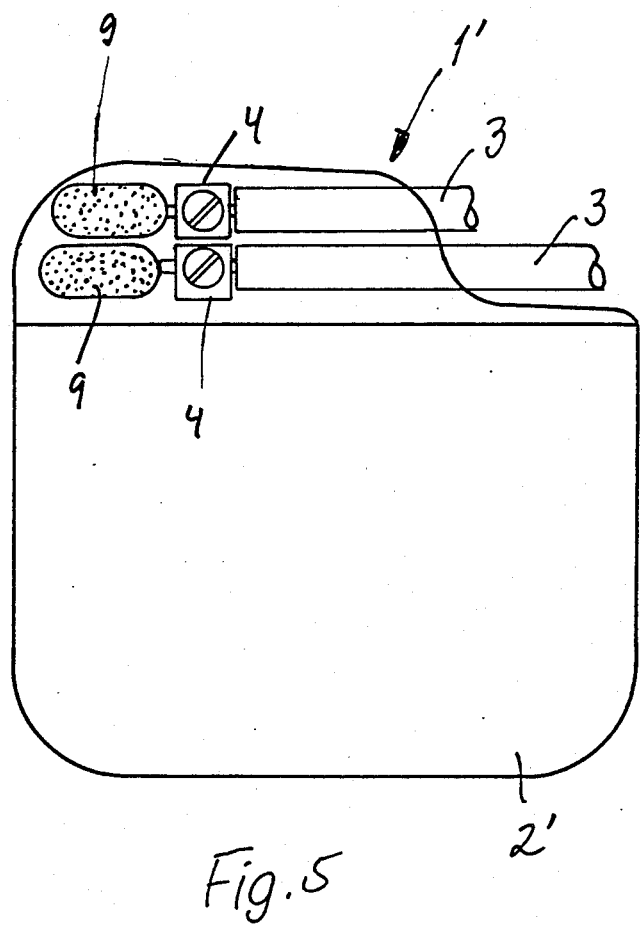
FIG. 5 is a side elevational view of a modified cardiac pacemaker with two discrete penetrable walls and two pulse transmitting leads.
Figure 7:
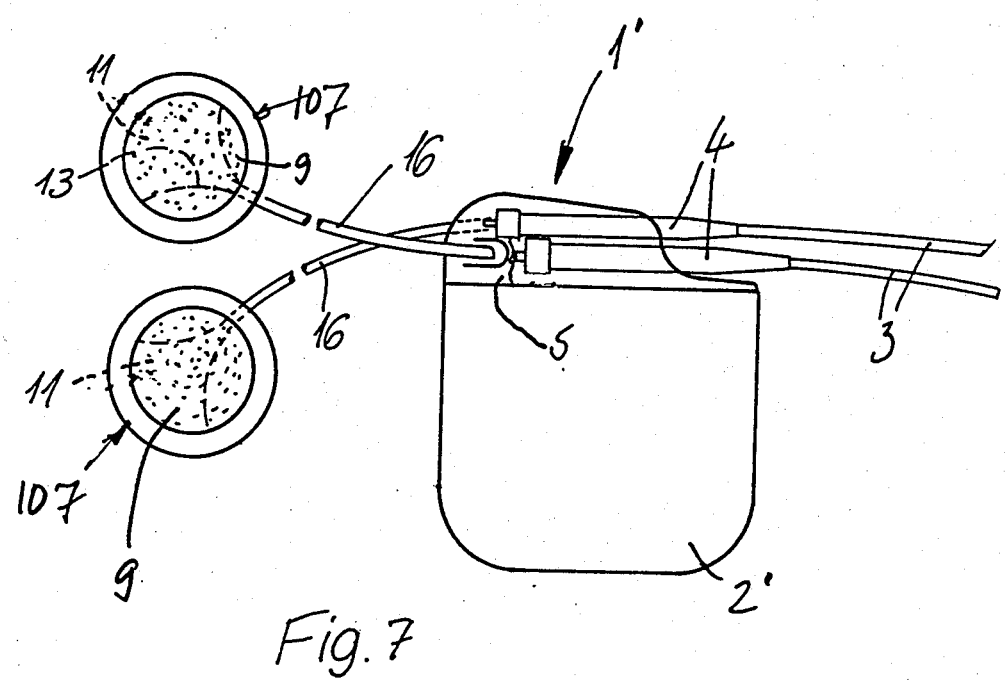
FIG. 7 is a side elevational view of a further pacemaker with two discrete penetrable walls which are remote from the housing of the pulse generator.

FIG. 1 shows a cardiac pacemaker 1 which comprises a subcutaneously implantable pulse generator 2 and at least one pulse transmitting lead 3 which normally transmits pulses to the heart. FIGS. 5 and 7 show embodiments with several implantable pulse transmitting leads 3.

Figure 2:
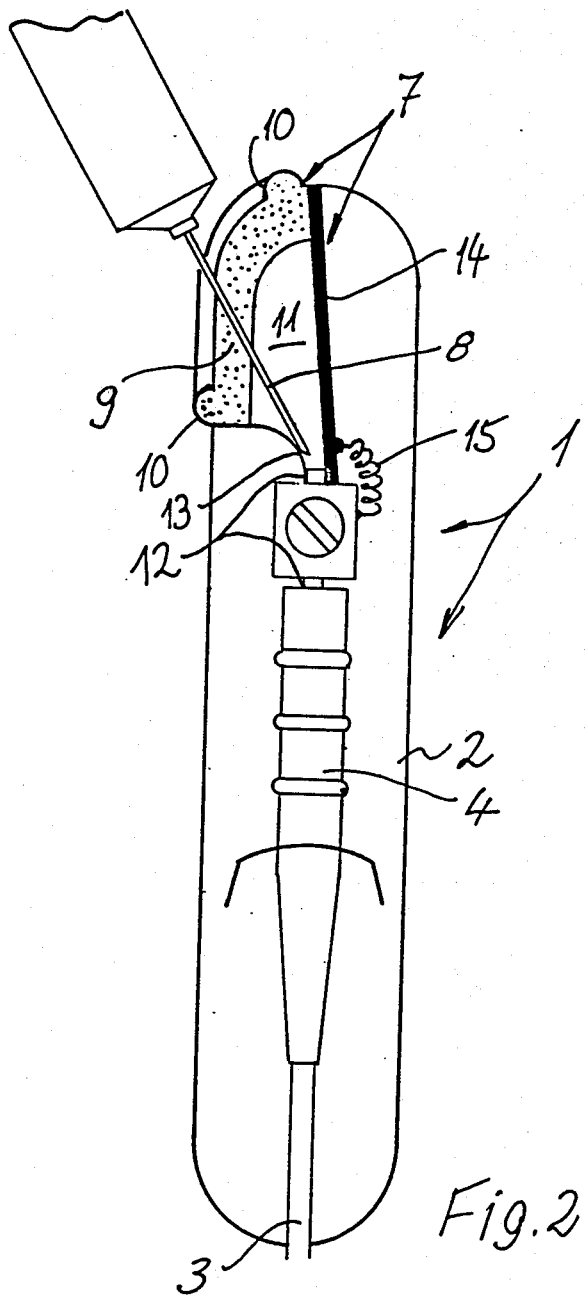
FIG. 2 is an enlarged plan view of the pacemaker, with the penetrable wall and a metallic portion of the housing of the pulse generator shown in section.

That terminal of the lead 3 which is shown in FIG. 1 is connected to the pulse transmitting output 5 of the generator 2 by a plug 4. In accordance with a feature of the invention, the region 7 directly behind the plug 4 and the output 5 is accessible to an instrument 8 whose working end must penetrate through the skin 6 (FIG. 3) of the patient and thereupon through a penetrable self-sealing wall 9 which forms part of the housing of the pulse generator 2. The instrument 8 of FIG. 1 is a cannula, and FIG. 1 further shows a second instrument 20 in the form of a screwdriver whose working end 21 must penetrate through the skin 6 in order to tighten or loosen the screw 4a of the connection including the plug 4. Reference may be had to the aforementioned U.S. Pat. No. 3,198,195. The wall 9 is implanted into the body of the patient beneath the skin 6 and preferably includes or constitutes a membrane consisting of or containing silicone or another neutral material which is compatible with the human body as an environment. The illustrated cannula 8 can be replaced by or used with an electrical conductor having a suitable stylet 22 (FIG. 3) to facilitate and simplify penetration through the skin 6 and the wall 9. The cannula 8 can be used to admit one or more medicaments. As best shown in FIG. 2, the wall 9 is reinforced by a marginal bead 10 which further serves to maintain the housing of the pulse generator 2 at a preselected location beneath the skin 6.

Figure 3:
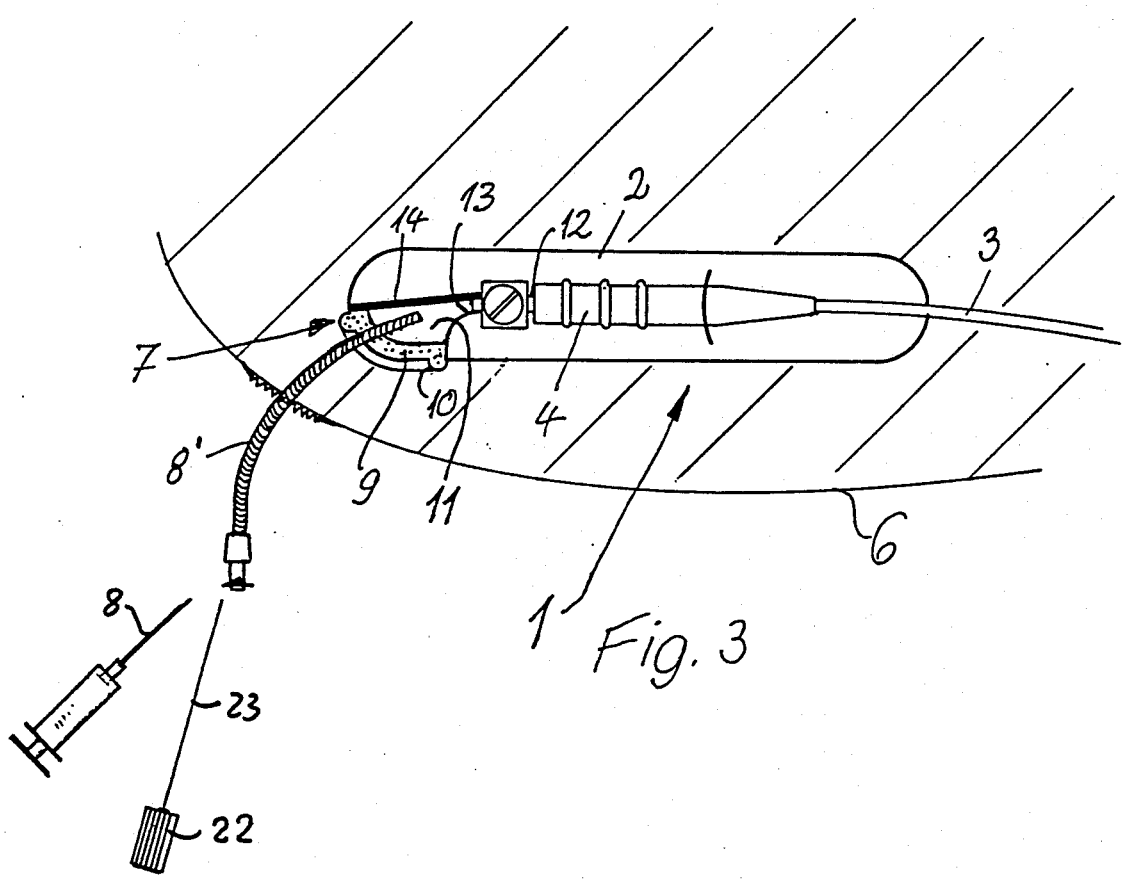
FIG. 3 is a smaller-scale view of the pacemaker of FIG. 2 with an instrument in the form of a space wound conductor coil which extends into the chamber behind the penetrable wall and can be used to facilitate the insertion of a cannula or the wire of a stylet.

The wall 9 and the adjacent portion of the housing of the pulse generator 2 define a chamber 11 which affords access to the output 5 by way of the wall 9. In the embodiments of FIGS. 1–6, the wall 9 is a component part of the housing of the pulse generator 2. One terminal of the lead 3 preferably extends to or can be reached by way of the chamber 11, and this lead can constitute a tube which enables the wire 23 of a stylet 22 (see also U.S. Pat. No. 4,393,883) to penetrate all the way into the heart of the patient after having penetrated through the skin 6 and the wall 9. The wire 23 of the stylet 22 can be used to connect the electrode at the other end of the lead 3 with a source of electric signals, with a source of medication or to adjust the position of the electrode. The wire 23 of the stylet 22 is introduced through the properly inserted cannula 8 or through a space wound conductor coil 8' (FIG. 3). However, it is equally within the purview of the invention to insert the wire 23 of a stylet 22 directly through the skin 6 and wall 9 and to thereupon push the wire 23 through the chamber 11 and into the lead 3. Such insertion of the wire 23 is possible and convenient because the chamber 11 is disposed between the wall 9 and the plug 4 of the connection which secures the lead 3 to the pulse generator 2. Moreover, the housing of the pulse generator 2 preferably includes a funnel 13 which defines a passage narrowing in a direction from the wall 9 toward the nearest end portion 12 of the lead 3 so that the surface which surrounds the funnel 13 guides the wire 23 of a stylet 22 or a cannula 8 on its way into the lead 3. The funnel 13 can be seen in each of FIGS. 1–4 and 6–8.

FIG. 2 further shows that the wall 9 is relatively thick. Such wall is preferably self-sustaining in that it tends to assume and retain a preselected configuration. This ensures that the volume of the chamber 11 remains substantially unchanged, for example, during penetration of the working end of the cannula 8 or the wire 23 of a stylet 22 through the skin 6 and thereupon through the wall 9.

The wall 9 defines the chamber 11 with an electrically conductive portion 14 of the housing of the pulse generator 2. The portion 14 can constitute or include a metallic plate, a netting, a latticework or any other suitable conductor which bounds a portion of the chamber 11 and is electrically connected with the output 5 and/or with the adjacent terminal of the lead 3, e.g., by way of the plug 4. As shown in FIG. 2, the portion 14 is connected with the plug 4 by a coiled wire-like conductor 15. FIG. 2 further shows that the conductor 15 is disposed at that side of the conductive portion 14 which faces away from the wall 9. The inner side of the portion 14 faces the inner side of the wall 9 so that it can be readily contacted by a conductor which is introduced into the chamber 11 by way of the cannula 8 or directly through the skin 6 and wall 9. This renders it possible to readily monitor the condition of the pulse generator 2 by a suitable measuring instrument or to supply additional impulses to the output 5 or to the portion 12 of the lead 3.

Figure 4:
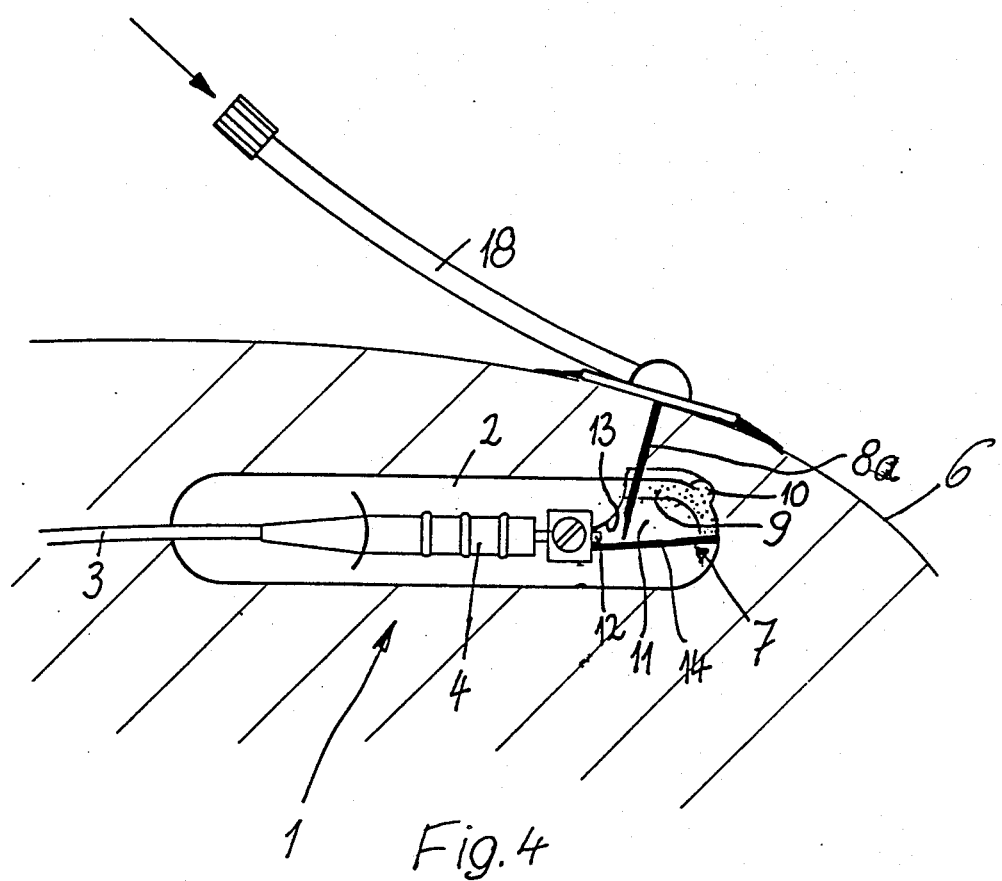
FIG. 4 illustrates the structure of FIG. 3 with a permanently implanted cannula as a substitute for the space wound conductor coil of FIG. 3.

FIG. 4 shows a permanently implanted cannula 8a which establishes communication between the chamber 11 and a flexible conduit 18 at the outer side of the skin 6. The conduit 18 can be used for continuous or intermittent infusion of medicaments or for introduction of the wire 23 of a stylet 22. The output of the cannula 8a can aim a jet of flowable material into the funnel 13 and thence into the channel of the lead 3. This ensures rapid infusion of predictable quantities of medicaments into the heart of the patient. Moreover, the conduit 18 can be readily detached from or reattached to the implanted cannula 8a.

FIG. 5 shows a modified pacemaker 1' with two leads 3, two plugs 4 and two discrete penetrable walls 9. Each of the walls 9 can afford access to the respective output of the pulse generator 2'. The walls 9 can bound two neighboring portions of a single chamber or portions of two discrete chambers.

Figure 6:
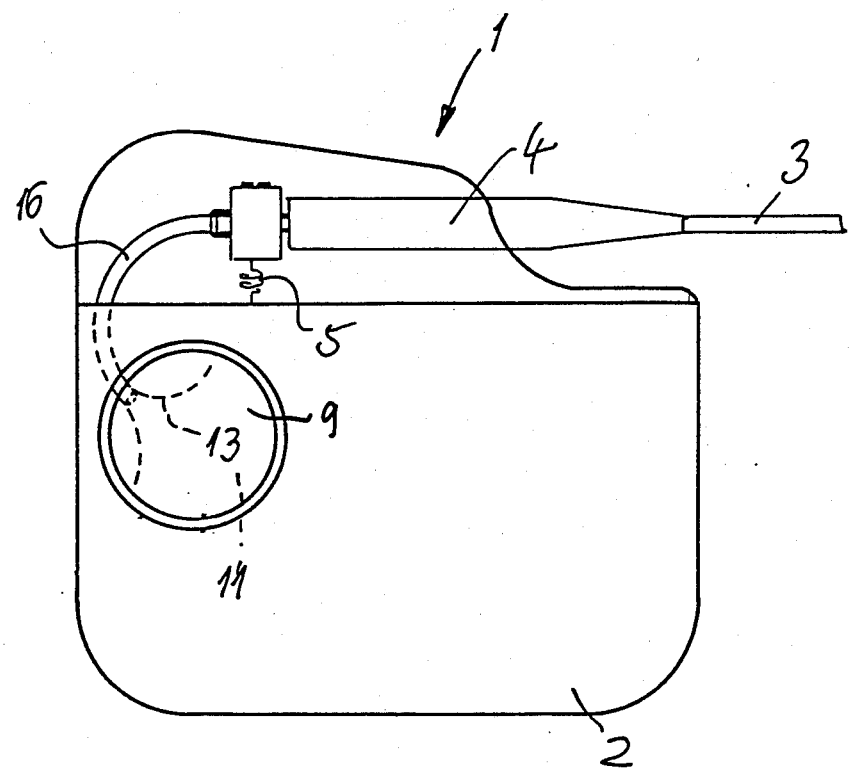
FIG. 6 is a side elevational view of a third pacemaker wherein the penetrable wall is laterally offset with reference to the adjacent terminal of the pulse transmitting lead.

FIG. 6 shows that the wall 9 need not be installed in line with but can be laterally offset from that terminal of the lead 3 which is connected to the pulse generator 2. This embodiment of the pacemaker further comprises an implanted subcutaneous conduit 16 which connects the chamber 11 behind the wall 9 with the plug 4 for the lead 3. An advantage of the pacemaker of FIGS. 5 and 6 is that the wall or walls 9 can be implanted in readily accessible positions even if the region behind the plug or plugs 4 is not as readily accessible. For example, the wall or walls 9 of FIGS. 5 and 6 can be nearer to the outer side of the skin than the housing of the pulse generator.

The pacemaker 1' of FIG. 7 comprises two penetrable walls 9 which are installed in two discrete casings 107 and are implanted into the body of the patient below the skin in readily accessible positions remote from the housing of the pulse generator 2' whose outputs 5 are connected with two discrete leads 3 by plugs 4. The housing of the pulse generator 2' is connected with the chambers 11 behind the walls 9 by two discrete conduits 16. One of the walls 9 will be penetrated by the wire of a stylet which is to be introduced into one of the leads 3 (e.g., into the lead carrying a ventricular electrode), and the other of the walls 9 will be penetrated by a wire which is to extend into the other lead 3 (e.g., into the lead carrying an atrial electrode).

Figure 8:
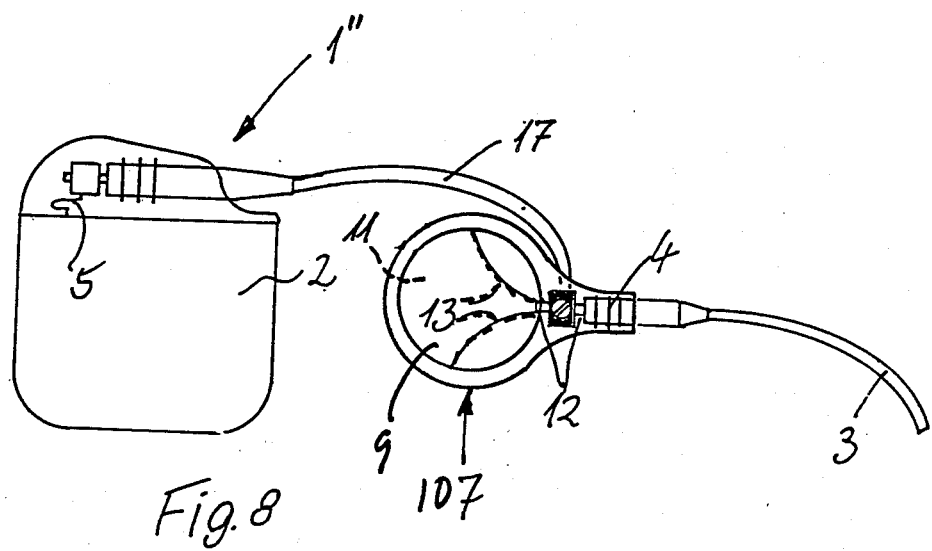
FIG. 8 is a side elevational view of still another pacemaker wherein the penetrable wall is remote from the housing of the pulse generator and the casing for such wall is connected with one terminal of the pulse transmitting lead.

FIG. 8 shows a pacemaker 1'' with a pulse generator 2, a single lead 3 whose plug 4 is connected to a casing 107 for a penetrable wall 9 defining with the casing a chamber 11 and a funnel 13 adapted to guide a cannula or a wire into the lead 3. The output 5 of the pulse generator 2 is connected with the end portion 12 by a flexible conductor 17 which is implanted into the body of the patient.

An important advantage of the improved pacemaker is that several of its components are readily accessible for monitoring, testing, adjustment or repair by the simple expedient of causing an instrument to penetrate through the wall 9 or through one of several walls 9 and to thus gain access to the chamber 11 behind the single wall 9 or behind the selected wall 9. As mentioned above, this renders it possible to admit medications directly to the heart of a patient, to transmit pulses to the conductive portion 14, to the end portion 12 of a lead 3, to the output or outputs 5, to a conduit 16 or to a conductor 17 (such conduits and conductors can be said to constitute extensions of the respective leads 3) and/or to mechanically influence one or more parts which are accessible by way of the chamber or chambers 11. The wall or walls 9 can be implanted in close proximity of the inner side of the skin 6 so that an instrument can reach the chamber 11 or a chamber 11 without passing through the tissue beneath the skin. The introduction of an instrument into the chamber 11 or into a selected chamber 11 of the improved pacemaker can be compared with the introduction of the needle of a hypodermic syringe but is normally less painful because the instrument is merely called upon to penetrate through the skin. Even such procedure can be dispensed with if a cannula (8a) is permanently implanted in a manner as shown in FIG. 4 or if such cannula is replaced with a permanently implanted space wound coil of the type shown in FIG. 3.

By way of example, the sensor of a measuring instrument can be introduced into the chamber 11 or into one of the chambers 11 in order to ascertain the locus of a defect, i.e., whether the defect is in a lead 3 or in the pulse generator 2 or 2'. The wall 9 automatically seals the chamber 11 from the surrounding tissue as soon as the instrument is withdrawn. Such types of walls are often used in suction-operated devices for evacuation of body fluids, e.g., from wounds.

The wire of a stylet can be introduced into a hollow lead to completely change or to merely adjust the position of the electrode. Furthermore, the wire of a stylet can be caused to transmit pulses to the output or outputs 5 and/or to the end portion or end portions 12 of one or more leads 3, either directly or by way of a metallic conductor such as the plate 14. This plate is inwardly adjacent the wall 9, i.e., the wall 9 is disposed between the skin and the plate 14 so that the tip of an instrument which has penetrated through the skin and thereupon through the wall 9 is bound to strike the plate 14. In many instances, the wall 9 and the associated plate 14 will completely surround the respective chamber 11. The same applies for the walls 9 and the casings 107 of the pacemaker which is shown in FIGS. 7 and 8.

An instrument can extend into the chamber 11 or into a selected chamber 11 of the improved pacemaker for extended intervals of time, e.g., for extensive testing of the pulse generator and/or other components of the pacemaker. Furthermore, the permanently implanted cannula 8a of FIG. 4 or the coil 8' of FIG. 3 can be used for continuous or longer-lasting infusion of medicaments.

Another important advantage of the improved pacemaker is its versatility. Thus, the provision of one or more walls 9 not only enables an expert to rapidly adjust one or more selected parts of the apparatus but such wall or walls further enable the expert to rapidly ascertain and locate the source or sources of malfunction and/or to extensively test the parts of the pacemaker without surgery and without the use of anesthetics. Extensive testing is desirable when the pulse generator and/or other parts of the pacemaker are suspected of short-lasting malfunctioning at randomly spaced intervals and/or when the reaction of a patient is not clear so that longer-lasting testing is the best way of ascertaining the reasons for intermittent malfunctions and/or for a patient's complaints. Once the cause of malfunction has been located, it can be eliminated in a simple way by using any one of a number of available implements or instruments. The wall or walls 9 render it possible to rapidly and painlessly adjust and/or repair a defective part of the pacemaker. Such wall or walls constitute a simple but highly effective means for permitting extensive testing of the parts of an implanted apparatus without surgery. This is particularly important to a cardiac patient since any surgery involving the implantation or removal of a pacemaker entails a potential and often substantial danger to the life of the patient.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A cardiac pacemaker comprising a subcutaneously implantable pulse generator having at least one pulse transmitting output; at least one subcutaneously implantable penetrable wall; and at least one implantable tubular lead connected with said output and having an open fluid receiving end adjacent said wall in implanted condition of said wall and said lead, said output and said open end being accessible to a percutaneous instrument in response to penetration of such instrument through the skin of the user of the pulse generator and thereupon immediately through said penetrable wall.

2. The pacemaker of claim 1, wherein said at least one lead is a pulse transmitting lead which is connected with said pulse generator to receive pulses from said output in implanted condition of said pulse generator and said lead.

3. The pacemaker of claim 2, wherein said instrument includes an electric conductor.

4. The pacemaker of claim 1, wherein said instrument includes a cannula.

5. The pacemaker of claim 1, wherein said wall contains a self-sealing material.

6. The pacemaker of claim 5, wherein said wall includes a membrane of a neutral material which is compatible with the human body as an environment.

7. The pacemaker of claim 6, wherein said membrane contains silicone.

8. The pacemaker of claim 1, wherein said wall comprises a self-sealing membrane and reinforcing means for said membrane.

9. The pacemaker of claim 8, wherein said reinforcing means comprises a marginal bead.

10. The pacemaker of claim 1, wherein said pulse generator includes a housing defining with said wall at least one chamber for said at least one output, said wall sealing said chamber from the body tissue surrounding said pulse generator in implanted condition of said housing and said wall, said open end being in communication with said chamber in implanted condition of said lead.

11. The pacemaker of claim 1, wherein said wall is substantially rigid and tends to assume and retain a predetermined shape.

12. The pacemaker of claim 1, wherein said pulse generator has a housing including an electrically conductive portion which is accessible to the instrument on penetration of the instrument through said wall, said lead being electrically connected with said output and/or with said conductive portion.

13. The pacemaker of claim 12, wherein said conductive portion includes a metallic plate.

14. The pacemaker of claim 12, wherein said conductive portion includes a metallic netting.

15. The pacemaker of claim 12, wherein said conductive portion includes a latticework.

16. The pacemaker of claim 12, wherein said conductive portion and said wall define at least one chamber for said output, said chamber being in communication with said open end in implanted condition of said housing, said wall and said lead.

17. The pacemaker of claim 1, wherein said at least one implantable lead is a pulse transmitting lead and further comprising means for electrically conencting said lead to said output, said pulse generator further comprising an electrically conductive portion connected with said connecting means and/or with said output and defining with said wall a chamber for said output, said chamber being adjacent said output and said connecting means, the open end of said lead being in communication with said chamber in implanted condition of said lead, said wall, said connecting means and said pulse generator.

18. The pacemaker of claim 17, wherein said pulse generator further comprises a funnel-shaped portion defining a narrowing passage extending from said chamber toward said open end.

19. The pacemaker of claim 1, wherein said wall is spaced apart from said pulse generator in implanted condition of said wall and said pulse generator, and further comprising an implantable casing defining with said wall a chamber which communicates with said open end in implanted condition of said lead and said casing and is accessible to the instrument upon penetration of the instrument through the skin and said wall, and means for connecting said chamber with said pulse generator.

20. The pacemaker of claim 19, wherein said connecting means comprises at least one electrical conductor.

21. The pacemaker of claim 19, wherein said connecting means comprises at least one conduit and said chamber communicates with said open end by way of said conduit.

22. The pacemaker of claim 19, further comprising means for electrically connecting said lead with said output.

23. The pacemaker of claim 1, further comprising at least one additional subcutaneously implantable penetrable wall and an additional implantable lead for said additional wall, said is accessible to the instrument upon penetration of the instrument through the skin and thereafter through additional lead having an end portion which said additional wall in implanted condition of said additional lead and said additional wall.

* * * * *